United States Patent [19]
Bjork et al.

[11] Patent Number: 5,565,455
[45] Date of Patent: Oct. 15, 1996

[54] METHOD FOR TREATING SUBSTANCE ABUSE DISORDERS

[75] Inventors: Anders Bjork, Bjarred; Gunnar Andersson, Lund, both of Sweden

[73] Assignee: Pharmacia AB, Stockholm, Sweden

[21] Appl. No.: 325,212

[22] PCT Filed: Apr. 19, 1993

[86] PCT No.: PCT/SE93/00339

§ 371 Date: Nov. 30, 1994

§ 102(e) Date: Nov. 30, 1994

[87] PCT Pub. No.: WO93/20821

PCT Pub. Date: Oct. 28, 1993

[30] Foreign Application Priority Data

Apr. 21, 1992 [SE] Sweden ................................ 9201239

[51] Int. Cl.$^6$ ........................................... A61K 31/495
[52] U.S. Cl. ................ 514/252; 514/218; 514/235.8; 514/248; 514/255; 514/357; 514/360; 514/810; 514/811; 514/812; 514/813
[58] Field of Search ..................... 514/218, 252, 514/235.8, 810, 811, 812, 813, 255, 248; 544/360, 357

[56] References Cited

U.S. PATENT DOCUMENTS

| | | | |
|---|---|---|---|
| 2,958,694 | 11/1960 | Janssen | 544/360 |
| 2,979,508 | 4/1961 | Janssen | 544/360 |
| 2,985,657 | 5/1961 | Janssen | 554/360 |
| 4,385,057 | 5/1983 | Björk et al. | 514/255 |
| 4,605,655 | 8/1986 | Yevich et al. | 514/252 |
| 4,766,215 | 8/1988 | Abou-Gharbia et al. | 544/357 |
| 4,937,245 | 6/1990 | Fex et al. | 514/252 |

FOREIGN PATENT DOCUMENTS

WO92/16211  10/1992  WIPO.

*Primary Examiner*—Kevin E. Weddington
*Attorney, Agent, or Firm*—Birch, Stewart, Kolasch & Birch, LLP

[57] ABSTRACT

A method for relief or prevention of a withdrawal syndrome resulting from addiction to a drug or substance of abuse and/or for the suppression of dependence on drugs or substances of abuse which comprises administering to a patient in need thereof an effective amount of a bisphenylalkylpiperazinde derivative, wherein said withdrawal syndrome comprises at least one of the symptoms selected from the group consisting of sleep disturbance, mood disturbance, and craving for the drug or substance of abuse.

8 Claims, No Drawings

METHOD FOR TREATING SUBSTANCE ABUSE DISORDERS

This application is a 371 of PCT/SE93/00339 filed 04/19/93.

FIELD OF THE INVENTION

The present invention relates to a new use of certain pyridyl- and pyrimidyl-substituted bisphenylalkylpiperazines in the treatment of substance abuse disorders. More particularly, this invention relates to the amelioration of withdrawal symptoms and to modify drug-seeking behaviour.

BACKGROUND OF THE INVENTION

Drug dependency is extremely difficult to escape. This is true whether the dependency is one based on ethanol, amphetamine, barbiturates, benzodiazepines, cocaine, nicotine, opioids, and phencyclidine or the like. There is a need, therefore for an agent decreasing or overcoming such addiction and, if possible reducing or eliminating the symptoms related to the withdrawal of such drugs or substances of abuse.

Different classes of neuronal receptors and neurotransmitters in the brain have been implicated in the complex mechanisms underlying for example the compulsive drinking of alcohol. Experimental findings have favoured the opioid, dopaminergic, serotonergic, and benzodiazepine receptor subtypes.

Based upon a large number of genetic and pharmacological studies, serotonin (5-ET) containing neurons in the limbic-midbrain and limbic-forebrain pathways are seemingly involved, in part, in the fundamental mechanisms underlying for example alcohol drinking.

A number of reports have established that 5-HT uptake blockers significantly attenuate ethanol intake in rats. For example, zimelidine (The Merck Index 11th Ed., No. 10024) was found to have a potent inhibitory effect on voluntary ethanol consumption in rats. In human trials, zimelidine was shown to increase the number of abstinent days and to produce a slight reduction in the number of daily drinks. There is ample evidence that serotonin is involved in the regulation of both food and fluid intake. Zimelidine was found to attenuate the ingestion of food and alcohol concomitantly. It is possible, therefore, that zimelidine's action is mediated through more global effects on consummatory behaviour rather than specific effects on ethanol reinforcement.

Buspirone (The Merck Index 11th Ed., No. 1493), a partial 5-HT$_{1A}$ agonist, has been found to be effective for the treatment of anxiety. Buspirone was reported to attenuate significantly the consumption of alcohol by monkeys. In a clinical trial comparing buspirone to placebo in alcohol-dependent individuals, there was a lower drop-out rate in the buspirone-treated group, which also reported fewer signs of craving.

Amperozide (The Merck Index 11th Ed., No. 612), a 5-HT$_2$ antagonist, was reported to significantly attenuate the intake of alcohol in rats without affecting neither consumption of food nor level of body weight.

SUMMARY OF THE INVENTION

It has now surprisingly been found that bisphenylalkylpiperazines of formula

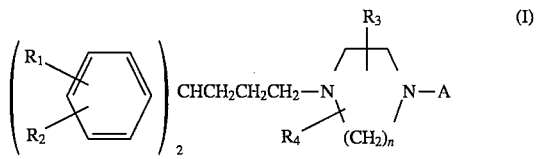

and the pharmaceutically acceptable acid addition salts thereof,
wherein $R_1$ and $R_2$ are the same or different and selected from hydrogen or halogen;
$R_3$ and $R_4$ are the same or different and selected from hydrogen or alkyl having 1 to 5 carbon atoms;
n is 2 or 3;
A is selected from the following pyrimidyl- or pyridyl-groups:

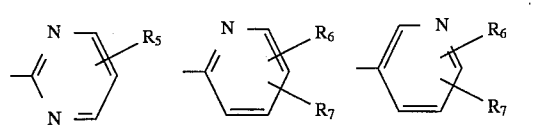

wherein $R_5$ is selected from hydrogen, alkyl having 1 to 5 carbon atoms or halogen; $R_6$ and $R_7$ are the same or different and selected from hydrogen, halogen, alkyl having 1 to 5 carbon atoms, alkoxy having 1 to 5 carbon atoms, hydroxy, cyano, nitro, trifluoromethyl, $COOR_8$, $CONR_9R_{10}$ or COB;
wherein $R_8$ is hydrogen or alkyl having 1 to 5 carbon atoms; $R_9$ and $R_{10}$ are the same or different and selected from hydrogen, alkyl having 1 to 5 carbon atoms or cycloalkyl having 3 to 8 carbon atoms;
B is selected from

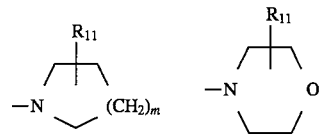

wherein m is 1, 2, 3, or 4; $R_{11}$ is selected from hydrogen or alkyl having from 1 to 5 carbon atoms;

and when used in the foregoing definitions the term alkyl is meant to include straight and branched hydrocarbon groups; the term alkoxy is meant to include straight and branched alkoxy groups; the term halogen is meant to include fluoro, chloro and bromo, are unexpectedly effective and specific in the treatment of individuals addicted to drugs or substances of abuse, suffering from symptoms related to withdrawal of such drugs or substances. This finding opens up a new method of treating dependence on drugs, such as alcohol, hallucinogens, minor tranquilizers, nicotine, opiates, and stimulants.

The aforementioned term "pharmaceutically acceptable acid addition salt" is meant to comprise these salts obtained by treating the base form of the active ingredients of formula (I) with appropriate acids, such as, for example, inorganic acids, e.g. hydrochloric acid, hydrobromic acid, sulfuric acid, nitric acid, and phosphoric acid, or organic acids, e.g. acetic acid, propanoic acid, glygolic acid, lactic acid, malonic acid, succinic acid, fumaric acid, tartaric acid, citric acid, and pamoic acid. Conversely, the salt form can be converted into the free base form by treatment with alkali.

The compounds of formula (I) as well as their preparation and pharmacological properties are known from U.S. Pat. No. 4,937,245.

DETAILED DESCRIPTION OF THE INVENTION

Twenty years of research has consistently demonstrated that drugs or substances that are abused by man are usually self-administered by laboratory animals. Ethanol, amphetamine, barbiturates, benzodiazepines, cocaine, nicotine, opioids, and phencyclidine and the like are just a few examples of substances abused by man and self-administered in animal models. The value of animal models for investigating the pharmacological and behavioural mechanisms underlying drug dependence has been repeatedly demonstrated. In fact, the animal models are our only recourse for the investigation of compounds to ameliorate or modify drug-seeking behaviour. In relation to this there is considerable experimental evidence supporting that a commonalty in the mechanism of the addictive process itself exists in the brain stem which underlies the predilection to abuse the above mentioned drugs.

The present invention relates to a method for treating substance abuse disorders by administering to a patient suffering from abuse a therapeutically effective amount of a compound of formula (I) or a pharmaceutically acceptable acid addition salt thereof. Specifically the invention relates to the relief or prevention of a withdrawal syndrome resulting from addiction to a drug or substance of abuse and/or for the suppression of dependence on drugs or substances of abuse.

Repeated administration to a subject of certain drugs such as alcohol, hallucinogens, minor tranquilizers, nicotine, opiates, and stimulants can lead to physical and/or psychological dependence upon that drug or substance. When the drug or substance of abuse is withdrawn from a dependent subject, the subject develops certain symptoms including sleep and mood disturbance and intense craving for the drug or substance of abuse. These symptoms may be collectively described as a withdrawal syndrome in connection with the present invention.

Although drug treatments for substance abuse disorders are available, these remain largely ineffective and unspecific and, therefore, improvement is needed. The anorexic and other effects of for example 5-HT reuptake blockers and buspirone constitute a major impediment to their consideration for clinical treatment. The compounds of formula (I) have been found to be both chemically and pharmacologically different from those drugs suggested hitherto for the treatment of drug dependence. A preferred compound is FG5893 (2-[4-[4,4-bis(4-fluorophenyl)butyl]-1-piperazinyl]-3-pyridinecarboxylic acid methyl ester dihydrochloride ethylat). FG5893 represents a new and novel class of psychotropic agents by having high affinity for both 5-HT$_{1A}$ and 5-HT$_2$ receptors in combination with potent 5-HT reuptake inhibiting properties.

The following example is intended to illustrate the present invention without limiting the scope thereof:

2-[4-[4,4-bis(4-fluorophenyl)butyl]-1-piperazinyl]-3-pyridinecarboxylic acid methyl ester 20 g (0.061 mole) of 1-[4,4-bis(p-fluorophenyl)butyl]-piperazine, 10 g (0.058 mole) of 2-chloro-3-pyridinecarboxylic acid methyl ester and 10 g (0.07 mole) of potassium carbonate were heated and stirred with 20 ml of toluene at 120° C. (temperature of oil bath) for 20 h.

After cooling, 40 ml of toluene was added. The mixture was filtered. The toluene solution was extracted with H$_2$O. The organic phase was dried over anhydrous Na$_2$SO$_4$ and evaporated to, yield 15 g (55%) of the free base of the title compound. The crude base was dissolved in ethanol and excess HCl in ethanol was added. Ether was added to precipitate 2-[4-[4,4-bis(4-fluorophenyl)butyl]-1-piperazinyl]-3-pyridinecarboxylic acid methyl ester dihydrochloride ethylat, m.p. 153°–66° C. (sintered).

The dihydrochloride salt was dissolved in hot H$_2$O. The solution was cooled to precipitate the hydrochloride salt. Recrystallization from aceton/ether yielded 2-[4-[4,4-bis(4-fluorophenyl)butyl]-1-piperazinyl]-3-pyridinecarboxylic acid methyl ester hydrochloride, m.p. 167°–687° C.

TABLE 1

Drug affinity for serotonergic receptor subtypes.

| Compound | K$_i$ (nM) | |
|---|---|---|
| | 5-HT$_{1A}$[a] | 5-HT$_2$[b] |
| FG5893 | 0.7 | 4.0 |
| Buspirone | 15 | 819 |
| Amperozide | 805 | 17 |

[a] Radioligand: $^3$H-8-OH-DPAT Tissue: Hippocampus
[b] $^3$H-Ketanserin Cerebral cortex

TABLE 2

Inhibition of reuptake of [$^3$H-5-HT] by synaptosomes from rat frontal cortex.

| Compound | IC$_{50}$ (μM) |
|---|---|
| FG5893 | 0.08 |
| Zimelidine | 0.12 |
| Buspirone | 22 |
| Amperozide | 0.32 |

According to the method of Shank, R. P. et al., J. Pharmacol. Exp. Ther. 242:74–84, 1987.

To further illustrate the useful pharmacological properties of FG5893, the effect of FG5893 administered systemically was determined in Sprague-Dawley rats induced to drink alcohol chronically by a series of intraperitoneal injections of cyan-amide according to experimental procedures described previously (Critcher, E. C. and R. D. Myers, Alcohol 4:347–353, 1987). Intakes of food and body weights were recorded.

FG5893 in a dose of 0.5, 1.0 and 2.5 mg/kg was administered twice a day for three consecutive days. Whereas control injections of saline were without effect on alcohol consumption, all doses of FG5893 significantly reduced the intake of alcohol in terms of both absolute g/kg and proportion of alcohol to total fluid intake. Further, the 1.0 and 2.5.mg/kg doses of FG5893 continued to suppress alcohol consumption over two 4-day tests immediately following the injection sequence and after a 40-day interval. Neither body weights nor intakes of food of the rats were affected by FG5893 either during or after its administration, suggesting a pharmacological specificity of action of this compound. This finding is notable because drugs that attenuate the preference for alcohol consumed in a concentration of pharmacological consequence typically impair the ingestion of food.

The compounds of formula (I) and their acid addition salts are therefore indicated for use in amelioration of withdrawal symptoms and in modifying drug-seeking behaviour.

Effective quantities of the compounds of formula (I) and their acid addition salts are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, patches for transdermal administration or sterile solutions for parenteral administration.

A suitable daily dose for use in the treatment of substance abuse disorders is contemplated to vary between 0.01 mg/kg to about 10 mg/kg body weight, in particular between 0.01 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

We claim:

1. A method for relief or prevention of a withdrawal syndrome resulting from addiction to a drug or substance of abuse and/or for the suppression of dependence on drugs or substances of abuse which comprises administering to a patient in need thereof an effective amount of a bisphenylalkylpiperazine of formula

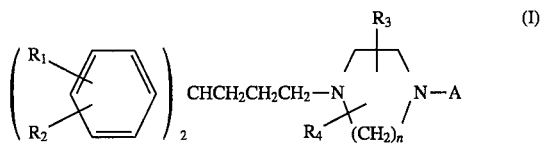

or a pharmaceutically acceptable acid addition salt thereof, wherein $R_1$ and $R_2$ are the same or different and selected from hydrogen or halogen;
$R_3$ and $R_4$ are the same or different and selected from hydrogen or alkyl having 1 to 5 carbon atoms;
n is 2 or 3;
A is selected from the following pyrimidyl- or pyridyl-groups:

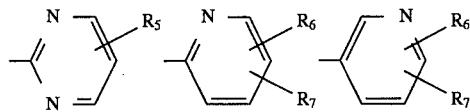

wherein $R_5$ is selected from hydrogen, alkyl having 1 to 5 carbon atoms or halogen; $R_6$ and $R_7$ are the same or different and selected from hydrogen, halogen, alkyl having 1 to 5 carbon atoms, alkoxy having 1 to 5 carbon atoms, hydroxy, cyano, nitro, trifuoromethyl, $COOR_8$, $CONR_9R_{10}$ or COB;

wherein $R_8$ is hydrogen or alkyl having 1 to 5 carbon atoms; $R_9$ and $R_{10}$ are the same or different and selected from hydrogen, alkyl having 1 to 5 carbon atoms or cycloalkyl having 3 to 8 carbon atoms;
B is selected from

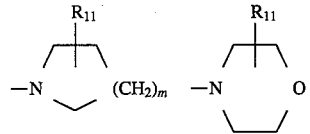

wherein m is 1, 2, 3, or 4; $R_{11}$ is selected from hydrogen or alkyl having from 10 to 5 carbon atoms;
and when used in the foregoing definitions, the term alkyl is meant to include straight and branched hydrocarbon groups; the term alkoxy is meant to include straight and branched alkoxy groups; the term halogen is meant to include fluoro, chloro and bromo; wherein said withdrawal syndrome comprises at least one of the symptoms selected from the group consisting of sleep disturbance, mood disturbance, and craving for the drug or substance of abuse.

2. The method of claim 1, wherein $R_1$ is hydrogen and $R_2$ is fluoro, wherein $R_3$ and $R_4$ are hydrogen, wherein n is 2, wherein A is

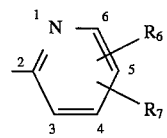

wherein $R_6$ is hydrogen and $R_7$ at the 3-position is $COOR_8$, and wherein $R_8$ is methyl; or a pharmaceutically acceptable salt thereof.

3. The method of claim 1, wherein n is 2.

4. The method of claim 1, wherein $R_1$ and $R_2$ are each a halogen.

5. The method of claim 1, wherein at least one of $R_6$ and $R_7$ represents $COOR_8$.

6. The method of claim 1, wherein $R_3$ and $R_4$ are hydrogen.

7. The method of claim 1, wherein said method suppresses the consumption of alcohol in a patient suffering from alcohol addiction.

8. The method of claim 1, wherein said bisphenylakylpiperazine is contained in an amount of 0.01 mg/kg to 1 mg/kg of body weight.

* * * * *